United States Patent [19]

Frances et al.

[11] Patent Number: 5,118,724

[45] Date of Patent: Jun. 2, 1992

[54] SILANE AND ORGANOPOLYSILOXANE CONTAINING A CYCLOPENTENYL RADICAL AND OBTAINABLE BY A MICHAEL REACTION

[75] Inventors: Jean-Marc Frances, Villeurbanne; Frederic Leising, Mornant, both of France

[73] Assignee: Rhone-Poulenc Chimie, Courbevoie, France

[21] Appl. No.: 616,935

[22] Filed: Nov. 21, 1990

[30] Foreign Application Priority Data

Nov. 21, 1989 [FR] France .................................. 1-15527

[51] Int. Cl.$^5$ .......................... C07F 7/18; C08G 77/20; C08G 77/44
[52] U.S. Cl. ...................................... 522/99; 522/172; 522/83; 556/465; 556/438; 556/410; 556/426; 528/34; 528/40; 528/41; 528/38
[58] Field of Search ............... 556/465, 438, 410, 426; 522/99, 172

[56] References Cited

U.S. PATENT DOCUMENTS

| | | | |
|---|---|---|---|
| 4,100,172 | 7/1978 | Mui et al. | 260/327 H |
| 4,107,390 | 8/1978 | Gordon et al. | 522/99 |
| 4,290,869 | 9/1981 | Pigeon | 522/172 |
| 4,526,954 | 7/1985 | Williams | 528/15 |
| 4,603,086 | 7/1986 | Fujii et al. | 522/99 |
| 4,697,026 | 9/1987 | Lee et al. | 522/99 |
| 4,992,261 | 2/1991 | Colas et al. | 556/438 |

FOREIGN PATENT DOCUMENTS 0170011 6/1985 European Pat. Off. .
0230342 1/1987 European Pat. Off. .

*Primary Examiner*—Marion E. McCamish
*Assistant Examiner*—Susan Berman
*Attorney, Agent, or Firm*—Burns, Doane, Swecker & Mathis

[57] ABSTRACT

The present invention proposes a silane and an organopolysiloxane containing a cyclopentenyl radical, characterized in that the silane or the organopolysiloxane has a radical Y of the formula:

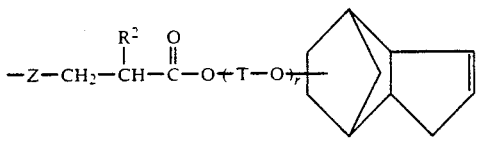

directly linked to the silicon atom.

The silanes according to the invention can be used as coupling and crosslinking agents, in particular in the compositions of acrylic paints.

The diorganopolysiloxanes according to the invention can be used as base polymer of a silicone composition which is crosslinkable to an elastomer, in particular by exposure to atmospheric oxygen.

13 Claims, No Drawings

SILANE AND ORGANOPOLYSILOXANE CONTAINING A CYCLOPENTENYL RADICAL AND OBTAINABLE BY A MICHAEL REACTION

The present invention relates to a silane and an organopolysiloxane containing a cyclopentenyl radical, as well as to the compositions which have a diorganopolysiloxane of this type as the base polymer and are crosslinkable to an elastomer, in particular by exposure to moisture and/or atmospheric oxygen and/or ultraviolet radiation.

Silicone compositions crosslinkable to an elastomer by a polycondensation reaction, through exposure to atmospheric moisture, are well known to those skilled in the art and are described in numerous patent documents.

Silicone compositions crosslinkable in a thin layer under ultraviolet radiation are also well known and comprise diorganopolysiloxane base polymers which generally carry epoxy, (meth)acrylate and mercapto groups.

More recently, there have been described silicone compositions crosslinkable with gaseous oxygen, in particular with atmospheric oxygen. The base polymers are either silicone oils having a mercapto group (see, for example, American Patents U.S. Pat. No. 252,392 and U.S. Pat. No. 268,655) or having a 1,4-pentadienylene group (American Patent U.S. Pat. No. 4,526,954).

The principal object of the present invention is to propose a silicone composition which is stable on storage in the absence of moisture, oxygen and ultraviolet, and which is crosslinkable to an elastomer by at least one crosslinking means chosen from amongst:

exposure of the silicone composition to atmospheric moisture, exposure of the silicone composition to gaseous oxygen, in particular atmospheric oxygen, and exposure of the silicone composition to ultraviolet.

To achieve this object, the present invention proposes, first of all, the silanes of the formula:

$$(X)_a Si(R^1)_b \quad \overset{Y}{|} \qquad (1)$$

in which:

$R^1$ is chosen from among monovalent hydrocarbon groups, optionally substituted by halogen atoms or cyano groups, X is a hydrolysable group and Y is a cyclopentenyl radical of the formula:

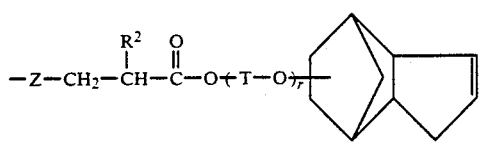

(2)

in which:

Z is a linear or branched divalent saturated hydrocarbon radical having from 1 to 6 carbon atoms, optionally interrupted by at least one hetero atom chosen from among S, N and O, T is a linear or branched divalent saturated $C_2$–$C_{20}$ hydrocarbon radical, $R^2$ is chosen from among a hydrogen atom and the methyl radical, a is chosen from among 0, 1, 2 and 3 and is preferably 2 or 3, b is chosen from among 0, 1 and 2, $a+b=3$, and r is 0 or 1.

The hydrocarbon radicals $R^1$ having from 1 to 10 C atoms and optionally substituted by halogen atoms or cyano groups comprise:

the alkyl and halogenoalkyl radicals having from 1 to 10 carbon atoms, such as the methyl, ethyl, propyl, isopropyl, butyl, pentyl, hexyl, 2-ethylhexyl, octyl, decyl, 3,3,3-trifluoropropyl, 4,4,4-trifluorobutyl and 4,4,4,3,3-pentafluorobutyl radicals, the cycloalkyl and halogenocycloalkyl radicals having from 1 to 10 carbon atoms, such as the cyclopentyl, cyclohexyl, methylcyclohexyl, propylcyclohexyl, 2,3-difluorocyclobutyl and 3,4-difluoro-5-methylcycloheptyl radicals, the alkenyl radicals having from 2 to 4 carbon atoms, such as the vinyl, allyl and but-2-enyl radicals, the mononuclear aryl and halogenoaryl radicals having from 6 to 10 carbon atoms, such as the phenyl, tolyl, xylyl, chlorophenyl, dichlorophenyl and trichlorophenyl radicals, and the cyanoalkyl radicals whose alkyl chains have from 2 to 3 carbon atoms, such as the β-cyanoethyl and α-cyanopropyl radicals.

The preferred radicals are the methyl, phenyl, vinyl and 3,3,3-trifluoropropyl radicals.

The hydrolysable radicals X, which may be identical or different, are more specifically chosen from among a halogen atom (preferably chlorine) and among N-substituted amino, N-substituted amido, N,N-disubstituted aminoxy, ketiminoxy, aldiminoxy, alkoxy, alkoxyalkyleneoxy, enoxy and acyloxy radicals.

Preferably, the radicals X correspond to the formulae:

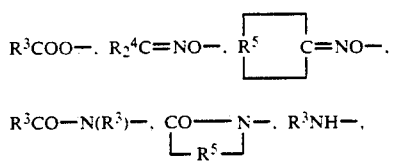

$R^3CO-N(R^3)-$, $CO-\overset{\phantom{R^5}}{\underset{R^5}{\vphantom{|}}}-N-$, $R^3NH-$, $R^6O-$, $R^6OR^7O-$ in which:

the symbol $R^3$, which may be identical or different, represents $C_1$–$C_{15}$ hydrocarbon radicals, the symbol $R^4$, which may be identical or different, represents $C_1$–$C_8$ hydrocarbon radicals, the symbol $R^5$ represents a $C_4$–$C_8$ alkylene radical, the symbol $R^6$ represents a $C_1$–$C_4$ alkyl radical and the symbol $R^7$ represents a $C_2$–$C_4$ alkylene radical.

The symbol $R^3$ represents $C_1$–$C_{15}$ hydrocarbon radicals which comprise:

the $C_1$–$C_{15}$ alkyl radicals such as the methyl, ethyl, propyl, 2-ethylhexyl, octyl, decyl, dodecyl and pentadecyl radicals, the $C_5$–$C_{10}$ cycloalkyl radicals such as the cyclopentyl, cyclohexyl, methylcyclohexyl, dimethylcyclohexyl, propylcyclohexyl and cycloheptyl radicals, the $C_6$–$C_{10}$ mononuclear aryl radicals such as the phenyl, tolyl and xylyl radicals, and the $C_2$–$C_{15}$ alkenyl radicals such as the octenyl, undecenyl and tetradecenyl radicals.

The symbol $R^4$ represents $C_1$–$C_8$ hydrocarbon radicals, which in particular comprise:

the $C_1$–$C_8$ alkyl radicals such as the methyl, ethyl, propyl, isopropyl, butyl, isobutyl, 2-ethylhexyl and octyl radicals, the $C_5$–$C_8$ cycloalkyl radicals such as the cyclopentyl, cyclohexyl and methylcyclohexyl radicals, and the $C_6$–$C_8$ mononuclear aryl radicals such as the phenyl, tolyl and xylyl radicals.

The symbol $R^6$ represents a $C_1$–$C_4$ alkyl radical such as the methyl, ethyl, propyl or butyl radicals.

The symbol $R^5$ represents a $C_4$–$C_8$ alkylene radical which can correspond to the formulae: —(CH$_2$)$_4$—, —(CH$_2$)$_5$—, —(CH$_2$)$_6$—, —(CH$_2$)$_7$—, —CH$_2$—CH(C$_2$H$_5$)(CH$_2$)$_3$—, —CH$_2$—CH$_2$—CH(CH$_3$)(CH$_2$CH$_2$—.

The symbol $R^7$ represents a $C_2$–$C_4$ alkylene radical which can correspond to the formulae: —(CH$_2$)$_2$—, —CH(CH$_3$)—CH$_2$, —CH(CH$_3$)CH$_2$CH$_2$—, —CH(CH$_3$)—CH(CH$_3$)—.

The preferred radicals X are the alkoxy radicals $R^6O$ and alkoxyalkyleneoxy radicals $R^6OR^7O$.

The silanes of the formula (1) can in particular be prepared by a MICHAEL reaction between an aminated silane of the formula:

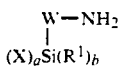

(3)

in which X, $R^1$, a and b have the meaning given above in connection with formula (1) and —W—NH— represents the radical Z, the definition of which is given in connection with formula (2), and dicyclopentadienyl (meth)acrylate of the formula:

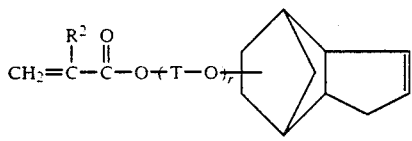

(4)

in which $R^2$, T and r have the meaning given in formula (2).

As concrete examples of organoaminosilanes of the formula (3) there may be mentioned those of the formulae given below, in which the organic group substituted by at least one amino radical is a hydrocarbon group:

H$_2$N(CH$_2$)$_3$Si(OC$_2$H$_5$)$_3$

H$_2$N(CH$_2$)$_4$Si(OCH$_3$)$_3$

H$_2$NCH$_2$CH(CH$_3$)CH$_2$CH$_2$SiCH$_3$(OCH$_3$)$_2$

-continued

H$_2$NCH$_2$Si(OCH$_3$)$_3$

H$_2$N(CH$_2$)$_2$NH(CH$_2$)$_3$Si(OCH$_3$)$_3$

H$_2$N(CH$_2$)$_2$NH(CH$_2$)$_3$Si(OCH$_2$CH$_2$OCH$_3$)$_3$

H$_2$N(CH$_2$)$_2$NH(CH$_2$)$_3$Si(OCH$_3$)$_2$
　　　　　　　　　　　　|
　　　　　　　　　　　OCH(CH$_3$)CH$_2$OCH$_3$

H$_2$N(CH$_2$)$_3$Si(OCH$_2$CH$_2$OCH$_2$CH$_3$)$_3$

H$_2$N(CH$_2$)$_2$NH(CH$_2$)$_3$SiCH=CH$_2$
　　　　　　　　　　　　|
　　　　　　　　　　　(OCH$_3$)$_2$

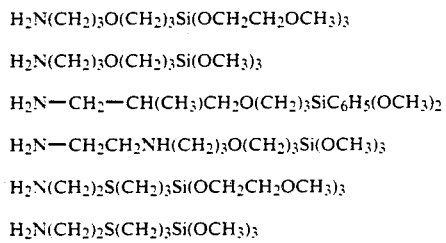

The preparation of these silanes features more especially in American Patents U.S. Pat. No. 2,754,311, U.S. Pat. No. 2,832,754, U.S. Pat. No. 2,930,809 and U.S. Pat. No. 2,971,864.

As further concrete examples of organoaminosilanes there may be mentioned those of the formulae given below, in which the organic group substituted by at least one amino radical is a hydrocarbon group carrying ether or thioether bonds:

H$_2$N(CH$_2$)$_3$O(CH$_2$)$_3$Si(OCH$_2$CH$_2$OCH$_3$)$_3$

H$_2$N(CH$_2$)$_3$O(CH$_2$)$_3$Si(OCH$_3$)$_3$

H$_2$N—CH$_2$—CH(CH$_3$)CH$_2$O(CH$_2$)$_3$SiC$_6$H$_5$(OCH$_3$)$_2$

H$_2$N—CH$_2$CH$_2$NH(CH$_2$)$_3$O(CH$_2$)$_3$Si(OCH$_3$)$_3$

H$_2$N(CH$_2$)$_2$S(CH$_2$)$_3$Si(OCH$_2$CH$_2$OCH$_3$)$_3$

H$_2$N(CH$_2$)$_2$S(CH$_2$)$_3$Si(OCH$_3$)$_3$

The preparation of these silanes features, in particular, in American Patents U.S. Pat. No. 3,341,563, U.S. Pat. No. 3,551,375, U.S. Pat. No. 3,598,853 and U.S. Pat. No. 3,488,373.

The dicyclopentadienyl meth(acrylates) of the formula (4) in which r=0 are described in particular in American Patents U.S. Pat. No. 2,414,089, U.S. Pat. No. 2,464,400 and U.S. Pat. No. 3,772,062, and those in which r=1 are described in particular in French Patent FR-A-2 399 994.

The MICHAEL reaction can in particular be carried out in accordance with the teaching of American Patent U.S. Pat. No. 3,033,815.

Typical silanes corresponding to the formula (1) are those of the formulae:

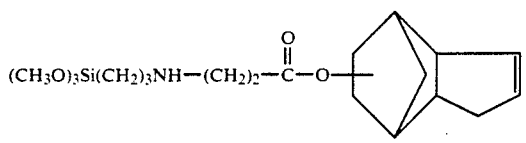

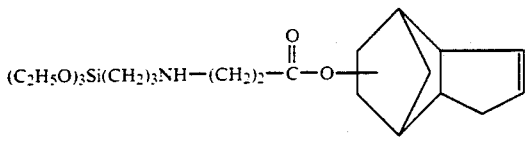

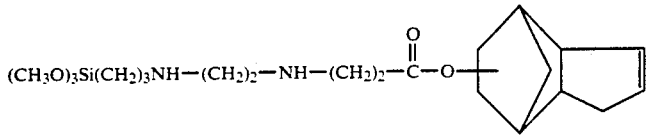

The present invention also proposes a polyorganosiloxane having, per molecule, at least one unit corresponding to the general formula

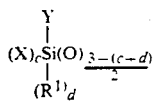   (5)

wherein
$R^1$, X and Y have the same meaning as that given above in connection with formula (1),
c is 0, 1 or 2,
d is 0, 1 or 2, and
c+d is at most equal to 2.

The polyorganosiloxane can furthermore optionally contain other siloxy units corresponding to the formula:

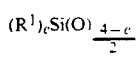   (6)

in which:
$R^1$ has the same meaning as in formula (1), and
e is chosen from among 0, 1, 2 and 3.

Preferably, $R^1$ is chosen from among the methyl, phenyl and vinyl radicals, with at least 80% of the number of $R^1$ radicals being methyl.

The polyorganosiloxanes according to the invention can accordingly have a linear, cyclic or branched structure.

The present invention more specifically proposes the random, sequenced or block diorganopolysiloxane copolymers of average formula:

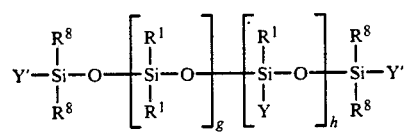   (7)

in which:
$R^1$, X and Y have the meaning given above,
Y' is chosen from among the radicals Y, $R^1$ and hydroxyl,
$R^8$ is chosen from among a radical $R^1$ and a radical X,
g is an integer between 0 and 1,000,
h is an integer between 0 and 50, and
if h=0, the two radicals Y' represent Y, and those of the formula:

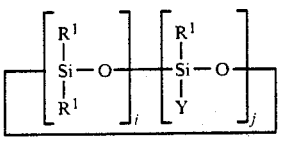   (8)

in which:
$R^1$ and Y have the meaning given above,
i is an integer between 0 and 9 inclusive,
j is an integer between 1 and 9 inclusive, and
i+j is between 3 and 10 inclusive.

The organopolysiloxanes of the formulae (5), (7) and (8) can be prepared in accordance with various processes.

A first process consists of hydrolysing and polycondensing the silanes of the formula (1), in which X is a halogen atom, preferably chlorine, in the optional presence of a halogenosilane, preferably a chlorosilane of the formula:

   (9)

where:
k=0, 1, 2 or 3,
l=1, 2, 3 or 4,
k+l=4, and
$R^1$ has the same definition as that given in connection with formula (1).

The use of a chlorosilane of the formula (9) makes it possible to incorporate units of the formula (6) in the organopolysiloxane of the formula (5). The polycondensation can be stopped by simple neutralization of the reaction mixture.

Where it is desired to obtain linear polymers of the formula (7) and/or cyclic polymers of the formula (8), the dichlorosilane $R^1YCl_2Si$, for example, is hydrolysed and polycondensed, optionally together with the dichlorosilane of the formula $R^1_2SiCl_2$.

Where the polycondensation is stopped by simple neutralization, a reaction mixture is obtained which contains polymers of the formula (7) blocked at each of their ends by a hydroxyl group or by the unit $R^1_2YSi$-$O_{0.5}$ if the silane $R^1_2YSiCl$ is used as an additional starting material.

It is also possible to stop the polycondensation by adding, at the end of the reaction, an organosilicon compound capable of reacting with the terminal hydroxyls of the polymer formed, of the formula (7); this organosilicon compound can correspond to the formulae:

The duration of the hydrolysis can be between a few seconds and several hours.

After hydrolysis, the aqueous phase is separated from the siloxane phase by any suitable physical means, generally by decanting and extracting with an organic solvent, such as isopropyl ether.

The siloxane phase can subsequently be washed with water and can then optionally be distilled to separate the linear polymers of the formula (7) from the cyclic polymers of the formula (8).

The polymers of the formula (7) can also be prepared by an equilibration process between a polydiorganopolysiloxane of the formula (7), where h is 0 and Y' is OH or $R^1$, and $R^8$ is $R^1$, with a silane of the formula (1), or a silane of the formula (3), followed, in the latter case, by a MICHAEL reaction with dicyclopentadienyl meth(acrylate).

Before carrying out this MICHAEL reaction, the starting material is thus a substantially linear diorganopolysiloxane having, in the chain, units of the formula:

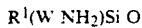

$$R^1(W\ NH_2)Si\ O$$

which are for example described in British Patent GB-A-1 306 680 and American Patent U.S. Pat. No. 4,412,035.

The present invention also more specifically proposes a sub-family of the polymers of the formula (7), corresponding to the formula:

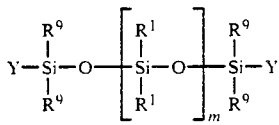

(10)

in which:

Y and $R^1$ have the same meaning given in connection with formula (1), the radicals $R^9$, which may be identical or different, are chosen from among the radicals $R^6O$ and $R^6OR^7O$, having the same definition as that given in connection with formula (1), and m is an integer between 0 and 2,000.

All the radicals $R^1$ are preferably methyl radicals.

The polymers of the formula (10) are prepared by condensation reaction of silanes of the formula:

$$(X)_3SiY \qquad (11)$$

where X is chosen from among the radicals $R^6O-$ and $R^6OR^7$, Y having the meaning given in connection with formula (1), with a di(hydroxy)diorganopolysiloxane of the formula:

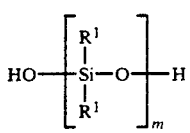

(12)

in which $R^1$ and m have the meaning given in connection with formula (10).

This polycondensation reaction is carried out in the presence of a catalytically effective quantity of a condensation catalyst.

As catalysts which may be used, there may in particular be mentioned:
potassium acetate: U.S. Pat. No. 3,504,051,
various inorganic oxides: FR-A-1 495 011,
organic derivatives of titanium: U.S. Pat. No. 4,111,890,
a titanate plus amine: U.S. Pat. No. 3,647,846,
an alkoxy-aluminium chelate: GB-A-2 144 758,
an N,N'-disubstituted hydroxylamine: FR-A-2 508 467,
a carboxylic acid plus amine: FR-A-2 604 713,
carbamates: EP-A-0 210 402,
organic compounds possessing an oxime group: FR-A-2 597 875.

It is recommended, within the scope of the present invention, to use, as the catalyst, lithium hydroxide of the formula LiOH or $LiOH.H_2O$, preferably employed in solution in an alcohol, in accordance with the teaching of French Patent Application 88/15 312, filed on 4th Nov. 1988 in the name of the Applicant Company.

According to this functionalization process, there are generally used from 1 to 60 moles of polyalkoxysilane of the formula (11) per mole of silanol ($=SiOH$) group of the polydiorganosiloxana of the formula (12), possessing a hydroxyl group linked to a silicon atom at each end of the chain, the excess of this polyalkoxysilane (11) being the greater, the higher the molecular weight of the polydiorganopolysiloxane of the formula (12).

By a catalytically effective quantity of lithium hydroxide there is to be understood a quantity such that the reaction rate is significantly improved and that the reaction temperature is as close as possible to ambient temperature.

In general, from 0.001 to 0.5 mole of lithium hydroxide is used relative to 1 mole of silanol group$=SiOH$ of the polydiorganosiloxane of the formula (12), it being understood that in order to have 1 mole of$=SiOH$, 0.5 mole of the polydiorganosiloxane of the formula (2) is required.

The process is carried out in the absence of moisture, for example in a closed reactor, equipped with a stirring system, in which a vacuum is set up, after which the air driven out is replaced by an anhydrous gas, for example by nitrogen.

The reactants and the catalyst are introduced into the reactor and when the functionalization reaction has ended, the catalyst is neutralized and, where appropriate, the reaction mixture obtained is devolatilized in order to remove therefrom the alcohol formed during the functionalization reaction and the excess of the functionalization agent [that is to say the silane of the formula (11)].

Numerous products, for example trichloroethyl phosphate or dimethylvinylsilyl acetate, can be used to neutralize the functionalization catalyst (the lithium hydroxide). However, it is preferred to use a silyl phosphate, such as, for example, those described in French Patent FR-A-2 410 004.

The devolatilization is carried out, for example under an absolute pressure of between 0.133 and 13.3 KPa.

The polymers of the formula (10) are more especially valuable because they can crosslink to an elastomer upon exposure to atmospheric humidity, by exposure to atmospheric oxygen, by ultraviolet radiation or by a combination of these three means.

The silanes of the formula (1) have a number of uses.

They can be used to prepare the organopolysiloxanes of the above formula (5), (7), (8) and (10).

They can also be used as coupling agents and as sizing agents.

They can be used as crosslinking agents in organopolysiloxane compositions which are cold-crosslinkable to an elastomer, and as adhesion promoters.

They can more especially be used as accelerators for the crosslinking, by oxygen and atmospheric humidity, of the conventional acrylic latices used as paints and coatings, in an amount of 0.1 to 10% by weight of silanes of the formula 1) relative to the weight of acrylate monomers present in the latex.

The branched polymers of the formula (5) can be used to form hard coatings after crosslinking with water and/or atmospheric oxygen, optionally in the presence of a condensation catalyst, which is a metal salt or a metal complex.

The linear polymers of the formulae (7) and (10) can more especially be used as base diorganopolysiloxane polymers, in a silicone composition, crosslinkable to an elastomer by at least one crosslinking means chosen from among:

exposure of the silicone composition to atmospheric humidity, exposure of the composition to gaseous oxygen, in particular atmospheric oxygen and exposure of the composition to ultraviolet.

These silicone compositions can be packaged in a single container and are stable on storage in the absence of moisture, oxygen and ultraviolet.

The present invention thus concerns an organopolysiloxane composition which is stable on storage in the absence of moisture, oxygen and ultraviolet and is crosslinkable to an elastomer by exposure to at least one crosslinking means chosen from among moisture, oxygen and ultraviolet radiation, characterized in that it comprises:

(A) 100 parts by weight of at least one polymer chosen from among one of the polymers of the formula (7) and the formula (10), given above, (B) 0 to 250 parts by weight of a mineral filler and (C) 0 to 5 parts of a hardening catalyst.

The mineral fillers (B) are used at the rate of 0 to 250 parts, preferably 20 to 200 parts, per 100 parts of the α,ω-di(hydroxy)diorganopolysiloxane polymers (A).

These fillers can be in the form of very finely divided products whose mean particle diameter is less than 0.1 micrometer. These fillers include pyrogenous silicas and precipitated silicas; their BET specific surface area is generally greater than 40 m²/g.

These fillers can also be in the form of more coarsely divided products, of mean particle diameter greater than 0.1 micrometer. As examples of such fillers there may be mentioned ground quartz, diatomaceous silicas, calcium carbonate, calcined clay, titanium oxide of the rutile type, oxides of iron, zinc, chromium, zirconium and magnesium, the various forms of alumina (which may or may not be hydrated), boron nitride, lithopone, barium metaborate, barium sulphate, and glass microspheres; their specific surface area is generally less than 30 m²/g.

These fillers (B) may have been surface-modified by treatment with the various organosilicon compounds usually employed for this purpose. Thus, these organosilicon compounds can be organochlorosilanes, diorganocyclopolysiloxanes, hexaorganodisiloxanes, hexaorganodisilazanes or diorganocyclopolysiloxanes (French Patents FR-A-1 126 884, FR-A-1 136 885 and FR-A-1 236 505 and British Patent GB-A-1 024 234). The treated fillers in the majority of cases contain from 3 to 30% of their weight of organosilicon compounds.

The fillers (B) can consist of a mixture of various types of fillers of different particle size: thus, for example, they can consist of 5 to 95% of finely divided silicas of BET specific surface area greater than 40 m²/g and of 95 to 5% of more coarsely divided silicas of specific surface area less than 30 m²/g or of treated or untreated calcium carbonate.

As condensation catalyst (C) it is possible to use, in particular, the monocarboxylic acid salts of metals such as barium, bismuth, cobalt, calcium, cerium, chromium, copper, iron, lead, magnesium, manganese, nickel, the rare earths, tin, zinc and zirconium. Other organic ligands may be bonded to the metals, such as chelate (acetylacetonate) and carbonyl ligands. The recommended catalysts are monocarboxylic acid salts of cobalt, tin, iron, lead and bismuth and more particularly cobalt 2-ethylhexanoate. Where a catalyst is used, amounts of 0.01 to 5 parts, preferably of 0.25 to 3 parts, by weight of metal salt per 100 parts of polymer A are generally very suitable.

The compositions according to the invention can furthermore contain from 0.05 to 5 parts of a photosensitizer per 100 parts of polymer (A).

As photosensitizer, it is recommended to use a mixture, preferably 50/50 by weight, of benzophenone and of 1-hydroxy-cyclohexyl phenyl ketone in the case of a composition free from fillers, or alternatively the MICHAEL ketone of the formula

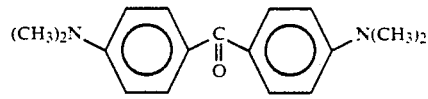

mixed, preferably 50/50, with benzophenone, if fillers are present.

However, other photosensitizers can be used and include, for example, 2-hydroxy-2-methyl-1-phenylpropanone, cyclohexanone, acetophenone, propiophenone, benzophenone, xanthone, fluorenone, benzaldehyde, fluorene, anthraquinone, triphenylamine, carbazole, 3-methylacetophenone, 4-methylacetophenone, 3-pentylacetophenone, 4-methoxyacetophenone, 3-bromoacetophenone, 4-allylacetophenone, p-diacetylbenzene, 3-methoxybenzophenone, 4-methylbenzophenone, 4-chlorobenzophenone, 4,4'-dimethoxybenzophenone, 4-chloro-4'-benzylbenzophenone, 3-chloroxanthone, 3,9-dichloroxanthone, 3-chloro-8-nonylxanthone, and the like.

The compositions according to the invention can furthermore contain the usual adjuvants or additives, conventionally used in the silicone elastomer compositions which are well known to those skilled in the art. Among these adjuvants there may in particular be mentioned the plasticizers, which can be silicone oils or organic plasticizers. In particular, the plasticizers described in American Patent U.S. Pat. No. 4,525,565 can be used.

Among the other adjuvants or additives there may in particular be mentioned colouring pigments, adhesion promoters, heat stabilizers, antioxidants, fluidization agents, thixotropic agents, perfumes, and the like.

In order to produce the compositions according to the invention, it is necessary to use an apparatus which permits the various essential constituents, to which the abovementioned adjuvants and additives are optionally added, to be mixed intimately with exclusion of moisture, gaseous oxygen and ultraviolet, with or without application of heat.

A more particularly recommended process is that which consists in introducing, in the stated sequence, the oil (A), the plasticizer where appropriate, the catalyst (C), the photosensitizer (D) where appropriate, and finally the filler (B), into a mixer, with heating where appropriate to a temperature of 20°-150° C., in the absence of atmospheric moisture.

Thereafter, degassing is preferably carried out under a reduced pressure of, for example, between 0.01 and 10 KPa.

The compositions according to the invention are storage-stable for at least 6 months and even one year, and can more particularly be used for jointing purposes in the building industry, for assembly of a great variety of materials (metals, plastics, natural and synthetic rubbers, wood, cardboard, earthenware, brick, ceramic, glass, stone, concrete and masonry components), for insulation of electrical conductors, for coating of electronic circuits, and for the preparation of moulds used for the manufacture of articles from synthetic resins or synthetic foams.

The compositions according to the invention can optionally be used after dilution with liquid organic compounds; the diluents are preferably conventional commercial products chosen from amongst:

aliphatic, cycloaliphatic and aromatic halogenated or non-halogenated hydrocarbons, such as cyclohexane and toluene, aliphatic and cycloaliphatic ketones such as methyl ethyl ketone, and esters such as ethyl acetate.

The amount of diluent in general remains low and is generally less than 50% by weight relative to the total weight of the composition.

The abovementioned dilutions of these compositions in organic diluents are more especially useful for impregnating thin layers of woven or non-woven articles or for coating metal foils or plastic or cellulose sheeting; however, they can be sprayed, for example by atomization with a paint gun, onto any substrates on which it is necessary to produce a coating having a thickness in the order of 5 to 300 μm. After the dilutions have been sprayed, the diluents evaporate and the compositions liberated harden to give a perfectly uniform rubbery film.

Furthermore, this elastomer film can serve as a non-toxic inert non-stick coating on various substrates in contact with foodstuffs, such as (1) wrapping papers for confectionery or frozen meats, (2) metal troughs useful for the preparation of ice cream and sorbets and (3) metal netting on which bread dough is placed and moulded, and which is introduced, with its content, into the ovens for baking the bread. It can also be employed as a non-stick and non-toxic coating on materials in contact with the human body, such as compresses and special bandages for burns.

In the subsequent and preceding texts, parts and percentages are by weight, unless stated otherwise.

The examples which follow illustrate the invention.

EXAMPLE 1

Preparation of a coupling agent of the formula

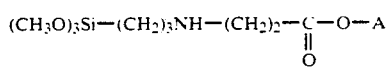

with A = 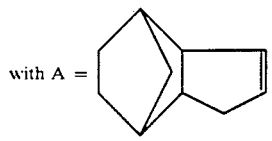

A coupling agent of the formula J/ is prepared by a MICHAEL reaction.

173 g (1 mole) of γ-aminopropyltrimethoxysilane and 204 g (1 mole) of dicyclopentadienyl acrylate are introduced at 20° C., under an inert atmosphere, into a glass reactor of 1 liter capacity, provided with a stirring system, a temperature probe and a reflux condenser.

The mixture is kept at 20° C. for 10 hours, with stirring. During the first hour, the temperature rises to 30° C.

$^1$H and $^{13}$C nuclear magnetic resonance (NMR) analysis confirms the structure of the product.

$^1$H NMR: solvent CDCl$_3$, reference TMS (tetramethylsilane)

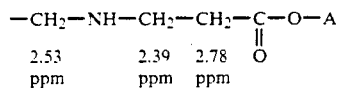

$^{13}$H NMR: solvent CDCl$_3$, reference TMS

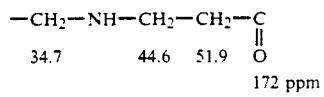

EXAMPLE 2

Functionalization of an α,ω-dihydroxypolydimethylsiloxane oil 800 g of an α,ω-dihydroxylated polydimethylsiloxane oil of average formula:

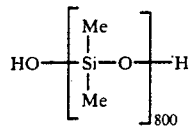

where
Me = methyl and
η = 40,000 mPa.s, representing about 30 mmoles of hydroxyl, are introduced into a 5 liter glass reactor equipped with a three-blade stirrer system.

15.30 g of the silane prepared in Example 1 (40 mmoles), followed by 0.38 g of a 10% strength solution of lithium hydroxide (LiOH) in methanol, representing 0.9 mmole, are added to this oil.

The mixture is stirred for 10 minutes at ambient temperature, and 0.68 g of an aqueous solution of phosphoric acid is then introduced into the functionalized oil.

An oil of average formula:

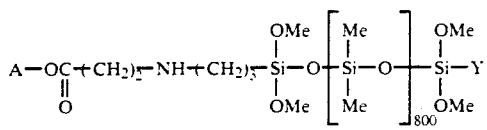

$$Y = -(CH_2)_3-NH-(CH_2)_2-\underset{\underset{O}{\|}}{C}-O-A$$

is obtained, in which A has the meaning given in Example 1, and which has a viscosity of 60,000 mPa.s, when stored with exclusion of air and light.

EXAMPLE 3

100 parts of the polymer obtained in Example 2, 100 parts of precipitated silica and 1 part of a 6% strength cobalt octoate solution are homogenized, with exclusion of atmospheric humidity and oxygen, in a three-blade mixer.

The single-component composition thus obtained is stored with exclusion of atmospheric moisture and oxygen in leakproof aluminium tubes; the contents of a tube are spread, in the form of a 2 mm thick layer, exposed to the atmosphere, on a polyethylene sheet.

The time (tp) for skin formation, also referred to as the time to achieve tack-free touch, and the demoulding time (td) required to be able to pull the elastomer off the sheet, are measured.

The deposited layer is converted to a rubbery film; 24 hours after depositing the layer, the elastomer film is lifted off and, after ageing for 1 day and for 7 days at ambient temperature, the tensometric properties of the elastomers are measured, namely:

the SHORE A hardness (SAH) according to standard specification NF-T-51 109, the tensile strength (TS) in MPa according to standard specification NF-T-46 002, the elongation at break (ED) in % according to standard specification NF-T-46 002, the modulus (Y.M.) in MPa for an elongation of 100%.

The results are as follows:
tp = 12 hours,
td = 72 hours,
After 1 day:
SAH = 10
After 7 days:
SAH = 15
EB = 86%
TS = 2 MPa.

EXAMPLES 4, 5, 6 AND 7

The procedure of Example 3 is repeated exactly except that the composition and the means of crosslinking are altered.

The results obtained are summarized in Table 1 below.

TABLE 1

|  | EX. 4A | EX. 4B | EX. 4C* | EX. 4C** |
|---|---|---|---|---|
| POLYMER B (parts) | 100 | 100 | 100 | 100 |
| AEROSIL COMBUSTION SILICA (parts) 150 m²/g | 8 | 0 | 8 | 8 |
| AEROSIL COMBUSTION SILICA 150 m²/g, dried for 3 h at 60° C. | 0 | 8 | 0 | 0 |
| COBALT OCTOATE (6% Co), parts | 0.05 | 0.05 | 0.05 | 0.05 |
| BENZOPHENONE (parts) | 0 | 0 | 0.125 | 0.125 |
| "MICHLER" KETONE (parts)*** | 0 | 0 | 0.125 | 0.125 |
| POURABILITY, mm. in 30 mn | 105 | 105 | 105 | 105 |
| SKIN FORMATION TIME (mn) | 25 | 25 | 15 | 30 |
| DEMOULDING (h) | 72 | 96 | 7 | greater than 4 days |
| SHORE A HARDNESS |  |  |  |  |
| 3 days | 2 | 0 | 5 | 0 |
| 7 days | 3 | 0 | 5 | 2 |
| TENSILE STRENGTH MPa | 0.22 | 0.2 | 0.63 | — |
| ELONGATION AT BREAK % | 606 | 420 | 380 | — |
| YOUNG'S MODULUS MPa | 0.2 | 0.2 | 0.3 | — |

*Exposure to atmospheric moisture and to sunlight
**Exposure to atmospheric moisture only
***"MICHLER" KETONE:

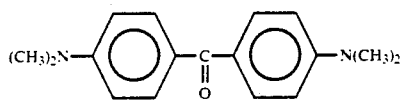

EXAMPLE 8

Condensation of an α,ω-dihydroxylated polydimethylsiloxane oil with an aminated silane 92.7 g of an α,ω-dihydroxylated polydimethylsiloxane oil containing 200 mmoles of hydroxyl, followed by 16.1 g of methyldimethoxy-N-aminoethylaminopropylsilane, representing 78 mmoles, are introduced into a 250 ml glass reactor equipped with a reflux condenser, a stirring and heating system, a temperature measuring system and a conical receiver dipped in a solid carbon dioxide/acetone bath and connected to a system for placing the apparatus under reduced pressure.

The mixture is heated at 80° C., with stirring, and the reactor is then placed under a reduced pressure, namely 0.133 KPa, for 360 minutes at 80° C.

4.18 g of methanol, representing 130 mmoles, are obtained.

²⁹Si, ¹H and ¹³C NMR spectroscopic analysis of the product obtained in the reactor is carried out.

Analysis by $^{29}$Si NMR in a CDCl$_3$ medium, relative to tetramethylsilane as a reference, makes it possible to record two types of signals, namely:

$$\text{RO}-\underset{\underset{\text{Me}}{|}}{\overset{\overset{\text{Me}}{|}}{\text{Si}}}-\text{O} = D^{OR} \; (-11.3 \text{ to } -14.7 \text{ ppm}) \quad 7.5 \text{ mol \%}$$

$$-\text{O}-\underset{\underset{\text{Me}}{|}}{\overset{\overset{\text{Me}}{|}}{\text{Si}}}-\text{O}- = D \text{ and modified } D \; (-19.4 \text{ to } -22.8 \text{ ppm}) \quad 92.5\%$$

representing a degree of conversion of the $D^{OH}$ units of 59%.

Accordingly, an oil of average formula:

$$\text{HO}-\underset{\underset{\text{Me}}{|}}{\overset{\overset{\text{Me}}{|}}{\text{Si}}}-\text{O}-\left[\underset{\underset{\text{Me}}{|}}{\overset{\overset{\text{Me}}{|}}{\text{Si}}}-\text{O}\right]_{21}\left[\underset{\underset{\underset{\underset{(CH_2)_2-NH_2}{|}}{NH}}{|}}{\overset{\overset{\text{Me}}{|}}{\text{Si}}}-\text{O}\right]_{1.7}\underset{\underset{\text{Me}}{|}}{\overset{\overset{\text{Me}}{|}}{\text{Si}}}-\text{OH}$$

and of viscosity 265 mPa.s is obtained.

EXAMPLE 9

MICHAEL addition reaction with a dicyclopentadiene acrylate 96.9 g of the polymer obtained in Example 8, representing 88 milliequivalents of NH$_2$, and 18.16 g of dicyclopentadiene acrylate, representing 89 mmoles, are introduced into the same reactor as that used in Example 8.

The whole is heated for 1 hour at 140° C.

An oil of average formula:

$$\text{HO}-\underset{\underset{\text{Me}}{|}}{\overset{\overset{\text{Me}}{|}}{\text{Si}}}-\text{O}-\left[\underset{\underset{\text{Me}}{|}}{\overset{\overset{\text{Me}}{|}}{\text{Si}}}-\text{O}\right]_{21}\left[\underset{\underset{\underset{W}{|}}{NH}}{\overset{\overset{\text{Me}}{|}}{\text{Si}}}-\text{O}\right]_{1.7}\underset{\underset{\text{Me}}{|}}{\overset{\overset{\text{Me}}{|}}{\text{Si}}}-\text{OH}$$

where $$W = CH_2-CH_2-NH-CH_2-CH_2-\underset{\underset{O}{||}}{C}-O-A$$

and

A has the meaning given in Example 1, is thus obtained.

In fact, $^1$H NMR shows the complete disappearance of the ethylenic protons at 5.7 and 6 and 6.3 ppm.

Equally, $^{13}$C NMR shows the disappearance of the signals attributed to the hydrogenated acrylic carbons at 129 and 129.7 ppm.

EXAMPLE 10

Crosslinking, exposed to atmospheric oxygen, or a dicyclopentadiene acrylate grafted oil Two compositions are produced from oil G obtained in Example 9.

| Composition 61: | 200 parts of oil G |
| | 200 parts of precipitated silica |
| | 20 parts of 6% strength cobalt octoate. |
| Composition 62: | 200 parts of oil G |
| | 300 parts of precipitated silica |
| | 20 parts of 6% strength cobalt octoate. |

Compositions 61 and 62 are applied in the form of films of 2.5 mm thickness onto a steel plate covered with a siliconized paper.

After 72 hours' exposure to atmospheric oxygen, the elastomers produced from compositions 61 and 62 are demouldable.

The elastomers are left for 7 days at ambient temperature.

The mechanical properties thus achieved are as follows:

| Composition $G_1$: | TS: 0.4 MPa |
| | EB: 81% |
| | YM: 0.5 MPa |
| Composition $G_2$: | TS: 0.5 MPa |
| | EB: 83% |
| | YM: 0.6 MPa |

EXAMPLE 12

MICHAEL reaction carried out at 20° C.

97.6 g of an α,ω-dihydroxylated polydimethylsiloxane oil containing 6.3 mmoles of hydroxyl and 0.649 g of the aminated silane used in Example 8 and introduced into a 250 ml reactor equipped with a blade stirrer system and capable of being placed under reduced pressure.

The mixture is heated under reduced pressure, namely 0.133 KPa, at 80° C. for 150 minutes; an oil of average formula:

$$\text{HO}-\underset{\underset{\text{Me}}{|}}{\overset{\overset{\text{Me}}{|}}{\text{Si}}}-\text{O}-\left[\underset{\underset{\text{Me}}{|}}{\overset{\overset{\text{Me}}{|}}{\text{Si}}}-\text{O}\right]_{800}\left[\underset{\underset{\underset{NH_2}{\big(}}{NH}}{\overset{\overset{\text{Me}}{|}}{\text{Si}}}-\text{O}\right]_{2}\underset{\underset{\text{Me}}{|}}{\overset{\overset{\text{Me}}{|}}{\text{Si}}}-\text{OH}$$

is obtained, to which 0.64 g, representing 3.15 mmoles, of dicyclopentadiene acrylate are added. The mixture is stirred for 15 hours at ambient temperature and an oil H of average formula:

$$\text{HO}-\underset{\underset{\text{Me}}{|}}{\overset{\overset{\text{Me}}{|}}{\text{Si}}}-\text{O}-\left[\underset{\underset{\text{Me}}{|}}{\overset{\overset{\text{Me}}{|}}{\text{Si}}}-\text{O}\right]_{400}\left[\underset{\underset{\underset{W}{|}}{NH}}{\overset{\overset{\text{Me}}{|}}{\text{Si}}}-\text{O}\right]_{2}\underset{\underset{\text{Me}}{|}}{\overset{\overset{\text{Me}}{|}}{\text{Si}}}-\text{OH} \quad \underline{H}$$

EXAMPLE 14 where W has the meaning given in Example 9, is obtained.

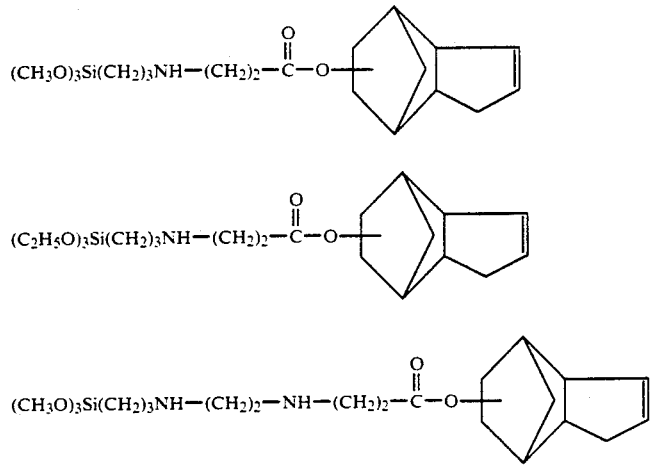

Two compositions are spread in the form of a 2.5 mm thick film:

| Composition H$_1$: | 200 parts of H |
| | 200 parts of precipitated silica |
| | 0.6 part of cobalt octoate |
| Composition H$_2$: | 200 parts of H |
| | 300 parts of precipitated silica |
| | 0.6 part of cobalt octoate. |

A skin formation time of 40 minutes is observed for H$_1$ and H$_2$.

We claim:

1. A silane of the formula

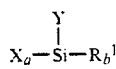 (1)

in which:
  R$^1$ is a monovalent hydrocarbon group, optionally substituted by halogen atoms or a cyano group,
  X is a hydrolyzable group and
  Y is a cyclopentenyl radical of the formula:

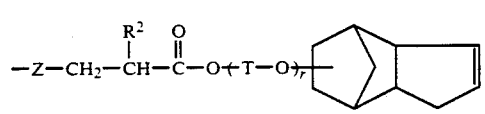 (2)

in which:
  Z is a linear or branched divalent saturated hydrocarbon radical having from 1 to 6 carbon atoms, optionally interrupted by at least one hetero atom comprising S, N or O,
  T is a linear or branched divalent saturated C$_2$–C$_{20}$ hydrocarbon radical,
  R$^2$ is a hydrogen atom or a methyl radical,
  a is 0, 1, 2 or 3,
  b is 0, 1 or 2,
  $a+b=3$, and
  r is 0 or 1.

2. The silane according to claim 1, wherein the radical X is a halogen atom, an N-substituted amino, N-substituted amido, N,N-disubstituted aminoxy, ketiminoxy, aldiminoxy, alkoxy, alkoxyalkyleneoxy, enoxy or acyloxy radicals.

3. Silanes of the formulae:

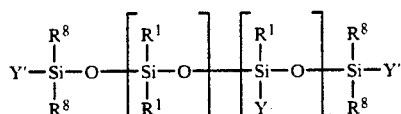

4. A polyorganosiloxane having, per molecule, at least one unit corresponding to the general formula:

$$(X)_c Si(O)_{\frac{3-(c+d)}{2}} (R^1)_d \quad (5)$$

wherein
  R$^1$, X and Y have the same meaning as that given above in connection with formula (1),
  c is 0, 1 or 2,
  d is 0, 1 or 2, and
  c+d is at most equal to 2.

5. A polyorganosiloxane according to claim 4, further comprising units $$(R^1)_e Si(O)_{\frac{4-e}{2}} \quad (6)$$

in which:
  R$^1$ has the same meaning as in formula (1), and
  e is 0, 1, 2 or 3.

6. Random, sequenced or block diorganopolysiloxane copolymers of the formula:

$$Y'-\underset{R^8}{\overset{R^8}{Si}}-O-\left[\underset{R^1}{\overset{R^1}{Si}}-O\right]_g-\left[\underset{Y}{\overset{R^1}{Si}}-O\right]_h-\underset{R^8}{\overset{R^8}{Si}}-Y'$$

in which:
  R$^1$, X and Y have the meaning given above,
  Y' is a radical Y, R$^1$ or hydroxyl,
  R$^8$ is a radical R$^1$ or a radical X,
  g is an integer between 0 and 1,000,
  h is an integer between 0 and 50, and
  if h=0, the two radicals Y' are Y, and those of the formula:

$$\left[ \begin{array}{c} R^1 \\ | \\ -Si-O \\ | \\ R^1 \end{array} \right]_i \left[ \begin{array}{c} R^1 \\ | \\ -Si-O \\ | \\ Y \end{array} \right]_j \quad (8)$$

in which:
R¹ and Y have the meaning given above,
i is an integer between 0 and 9 inclusive,
j is an integer between 1 and 9 inclusive, and
i+j is between 3 and 10 inclusive.

7. A polydiorganosiloxane according to claim 6, corresponding to the formula:

$$Y-\underset{\underset{R^9}{|}}{\overset{\overset{R^9}{|}}{Si}}-O\left[\underset{\underset{R^1}{|}}{\overset{\overset{R^1}{|}}{Si}}-O\right]_m\underset{\underset{R^9}{|}}{\overset{\overset{R^9}{|}}{Si}}-Y \quad (10)$$

in which:
Y and R¹ have the meaning given in connection with formula (1),
the radicals R⁹, which may be identical or different, are the radicals R⁶O or R⁶OR⁷O, with the symbol R⁶ representing a $C_1-C_4$ alkyl radical and the symbol R⁷ representing a $C_2-C_4$ alkylene radical, and m is an integer between 0 and 2.000.

8. An organopolysiloxane composition comprising:
(A) at least one polydiorganosiloxane as defined in claim 6 or 7,
(B) optionally a mineral filler and
(C) optionally a catalytically effective amount of a hardening catalyst.

9. A composition according to claim 8, wherein the hardening catalyst is based on iron, manganese or tin.

10. A composition according to claim 8, further comprising a photosensitizer.

11. A composition according to claim 10, wherein the photosensitizer has the formula:

$(CH_3)_2N-\langle\bigcirc\rangle-\overset{\overset{O}{\|}}{C}-\langle\bigcirc\rangle-N(CH_3)_2$ (MICHLER ketone)

$\langle\bigcirc\rangle-\overset{\overset{OH}{|}}{\underset{\underset{O}{\|}}{C}}-\langle\bigcirc\rangle$ (1-hydroxy-cyclohexyl phenyl ketone)

$\langle\bigcirc\rangle-\overset{\overset{}{}}{\underset{\underset{O}{\|}}{C}}-\langle\bigcirc\rangle$ (benzophenone)

12. A composition according to claim 8 comprising:
(A) 100 parts by weight said at least one polydiorganosiloxane;
(B) 0 to 250 parts by weight of said mineral filler; and
(C) 0 to 3 parts of said hardening catalyst.

13. A composition according to claim 12 further comprising from 0.05 to 5 parts of a photosensitizer per 100 parts of polymer (A).

* * * * *